(12) United States Patent
Dolan et al.

(10) Patent No.: US 6,444,012 B1
(45) Date of Patent: Sep. 3, 2002

(54) SELECTIVE REMOVAL OF NITROGEN FROM NATURAL GAS BY PRESSURE SWING ADSORPTION

(75) Inventors: William B. Dolan, Yardley, PA (US); Kenneth F. Butwell, Newburgh, NY (US)

(73) Assignee: Engelhard Corporation, Iselin, NJ (US)

(*) Notice: Subject to any disclaimer, the term of this patent is extended or adjusted under 35 U.S.C. 154(b) by 4 days.

(21) Appl. No.: 09/699,664

(22) Filed: Oct. 30, 2000

(51) Int. Cl.[7] ............................................. B01D 53/047
(52) U.S. Cl. ................ 95/99; 95/105; 95/115; 95/130; 95/143; 95/901; 95/902
(58) Field of Search .................. 95/96–106, 114, 95/115, 130, 143–148, 901, 902

(56) References Cited

U.S. PATENT DOCUMENTS

| | | |
|---|---|---|
| 2,656,010 A | 10/1953 | Thodos |
| 2,843,219 A | 7/1958 | Habgood |
| 2,918,140 A | 12/1959 | Brooks |
| 3,279,153 A * | 10/1966 | Basmadjian et al. ...... 95/130 X |
| 3,430,418 A | 3/1969 | Wagner |
| 3,738,087 A | 6/1973 | McCombs |
| 4,190,424 A | 2/1980 | Armond et al. |
| 4,512,780 A | 4/1985 | Fuderer |
| 4,588,427 A | 5/1986 | Yao et al. |
| 4,589,888 A | 5/1986 | Hiscock et al. |
| 4,784,672 A * | 11/1988 | Sircar ........................ 95/98 X |
| 4,938,939 A | 7/1990 | Kuznicki |
| 4,964,888 A | 10/1990 | Miller |
| 4,964,889 A | 10/1990 | Chao |
| 5,174,796 A | 12/1992 | Davis et al. |
| 5,224,350 A * | 7/1993 | Mehra ........................ 95/96 X |
| 5,248,322 A | 9/1993 | Kumau |
| 5,354,346 A * | 10/1994 | Kumar ..................... 95/130 X |
| 5,382,280 A * | 1/1995 | Choe et al. .................... 95/98 |
| 5,536,300 A | 7/1996 | Reinhold, III et al. |
| 5,669,958 A | 9/1997 | Baker et al. |
| 5,803,953 A | 9/1998 | Rojey et al. |
| 5,989,316 A | 11/1999 | Kuznicki et al. |
| 5,993,517 A * | 11/1999 | Chen et al. .................... 95/98 |
| 6,068,682 A | 5/2000 | Kuznicki et al. |
| 6,197,092 B1 | 3/2001 | Butwell et al. |
| 6,210,466 B1 * | 4/2001 | Whysall et al. ........... 95/130 X |
| 6,290,751 B1 * | 9/2001 | Ragil et al. ............... 95/130 X |
| 6,315,817 B1 * | 11/2001 | Butwell et al. ................ 95/96 |

FOREIGN PATENT DOCUMENTS

| | | |
|---|---|---|
| EP | 0302658 | 7/1988 |
| EP | 0297542 | 1/1989 |
| WO | WO99/32222 | 1/1999 |
| WO | WO99/32404 | 1/1999 |

* cited by examiner

*Primary Examiner*—Robert H. Spitzer
(74) *Attorney, Agent, or Firm*—Stuart D. Frenkel

(57) ABSTRACT

A pressure swing adsorption process for the separation of nitrogen from natural gas utilizes two separate pressure swing adsorption stages, the first containing a hydrocarbon-selective adsorbent and the second containing a nitrogen-selective adsorbent. In the process, the product stream from the first pressure swing adsorption unit contains a natural gas stream having a reduced hydrocarbon content and the product stream from the second pressure swing adsorption unit is a natural gas stream having a reduced nitrogen concentration. The product from the second pressure swing adsorption unit is used to desorb the hydrocarbons from the first pressure swing adsorption unit so as to add the hydrocarbons, which have heat value to the product natural gas stream. Periodically, heating the nitrogen-selective adsorbent with heated product stream from the second pressure swing adsorption unit has been found to improve the capacity of the nitrogen-selective adsorbent to adsorb nitrogen.

38 Claims, 2 Drawing Sheets

SELECTIVE REMOVAL OF NITROGEN FROM NATURAL GAS BY PRESSURE SWING ADSORPTION

FIELD OF THE INVENTION

This invention relates to the purification of natural gas, and, more particularly, to the removal of nitrogen from natural gas by use of a molecular sieve in a novel pressure swing adsorption (PSA) process.

BACKGROUND OF THE INVENTION

The removal of nitrogen from natural gas is of considerable importance inasmuch as nitrogen is present to a significant extent. Nitrogen contamination lowers the heating value of the natural gas and increases the transportation cost based on unit heating value.

Applications aimed at removing nitrogen and other impurities from natural gas streams provide significant benefits to the U.S. economy. In 1993, the Gas Research Institute (GRI) estimated that 10–15% (~22 trillion cubic feet) of the natural gas reserves in the U.S. are defined as sub-quality due to contamination with nitrogen, carbon dioxide, and sulfur. Most of these reserves, however, have discounted market potential, if they are marketable at all, due to the inability to cost effectively remove the nitrogen. Nitrogen and carbon dioxide are inert gases with no BTU value and must be removed to low levels (<4% typically) before the gas can be sold.

Concurrently, the U.S. has proven reserves of natural gas totaling 167 trillion cubic feet. Over the past five years, annual consumption has exceeded the amount of new reserves that were found. This trend could result in higher cost natural gas and possible supply shortages in the future. As the U.S. reserves are produced and depleted, finding new, clean gas reserves involves more costly exploration efforts. This usually involves off shore exploration and/or deeper drilling onshore, both of which are expensive. Moreover, unlike crude oil, it is not economical to bring imports of natural gas into North America, therefore pricing of natural gas could be expected to rise forcing end users to seek alternative fuels, such as oil and coal, that are not as clean burning as gas. While base consumption for natural gas in the U.S. is projected to grow at 2–3% annually for the next ten years, one segment may grow much more rapidly. Natural gas usage in electric power generation is expected to grow rapidly because natural gas is efficient and cleaner burning allowing utilities to reduce emissions. Accordingly, there is a need to develop a cost-effective method of upgrading currently unmarketable sub-quality reserves in the U.S. thereby increasing the proven reserve inventory.

Methods heretofore known for purification of natural gas, in particular, nitrogen removal, may be divided roughly into three classifications:

(a) Methods involving fractional distillation at low temperature and (usually) high pressure, i.e. cryogenics. Since nitrogen has a lower boiling point than methane and the other hydrocarbons present in natural gas, it may be removed as a gas on liquefying the remaining constituents, which are then revaporized.

(b) By selective adsorption of the methane and higher hydrocarbons on an adsorbent such as activated charcoal. The adsorbed gases are then desorbed to give a gas free of nitrogen.

(c) Miscellaneous processes involving selective diffusion through a series of organic membranes, formation of lithium nitride by treatment with lithium amalgam, absorption of the nitrogen in liquid ammonia or in liquid sulphur dioxide.

The principal disadvantage of the fractional distillation and adsorption processes is that they remove the major component, methane, from the minor component, nitrogen, instead of the reverse. In cryogenic processing, almost the entire volume of natural gas must be refrigerated, usually compressed, and then heated again. Accordingly, cryogenic processing is expensive to install and operate, limiting its application to a small segment of reserves. Cryogenic technology is believed only capable of cost effectively purifying reserves, which exceed 50,000,000 standard cubic feet of gas per day and as well having nitrogen contamination level of 15% or more. Gas reserves that do not fit these criteria are not currently being purified. The potential value of this gas is totally lost as the wells are usually capped. The processes suggested under paragraph (c) above are handicapped by an unsatisfactory degree of separation or by the use of very expensive materials.

In smaller-scale natural gas operations as well as in other areas such as synthesis gas and coke oven gas processing, adsorption processes can be especially well suited. The adsorption capacities of adsorption units can, in many cases, be readily adapted to process gas mixtures of varying nitrogen content without equipment modifications, i.e. by adjusting adsorption cycle times. Moreover, adsorption units can be conveniently skid-mounted, thus providing easy mobility between gas processing locations. Further, adsorption processes are often desirable because more than one component can be removed from the gas. As noted above, nitrogen-containing gases often contain other gases that contain molecules having smaller molecular dimensions than nitrogen, e.g., for natural gas, carbon dioxide, oxygen and water, and for coke oven gas, carbon monoxide.

U.S. Pat. No. 2,843,219 discloses a process for removing nitrogen from natural gas utilizing zeolites broadly and contains specific examples for the use of zeolite 4A. The process disclosed in the patent suggests use of a first nitrogen selective adsorbent zeolite in combination with a second methane selective adsorbent. The molecular sieve adsorbent for removing nitrogen is primarily regenerated during desorption by thermal swing. A moving bed adsorption/desorption process is necessary for providing sufficient heat for the thermal swing desorption. The moving bed process specifically disclosed in this patent is not practical and it does not provide a cost efficient method for the separation of nitrogen from natural gas in view of high equipment and maintenance costs and degradation of the adsorbent by attrition due to contact with the moving adsorbent portables.

Despite the advantageous aspects of adsorption processes, the adsorptive separation of nitrogen from methane has been found to be particularly difficult. The primary problem is in finding an adsorbent that has sufficient selectivity for nitrogen over methane in order to provide a commercially viable process. In general, selectivity is related to polarizability, and methane is more polarizable than nitrogen. Therefore, the equilibrium adsorption selectivity of essentially all known adsorbents such as large pore zeolites, carbon, silica gel, alumina, etc. all favor methane over nitrogen. However, since nitrogen is a smaller molecule than methane, it is possible to have a small pore zeolite, which adsorbs nitrogen faster than methane. Clinoptilolite is one of the zeolites, which has been disclosed in literature as a rate selective adsorbent for the separation of nitrogen and methane.

U.S. Pat. No. 4,964,889 discloses the use of natural zeolites such as clinoptilolites having a magnesium cation content of at least 5 equivalent percent of the ion-exchangeable cations in the clinoptilolite molecular sieve for the removal of nitrogen from natural gas. The patent discloses that the separation can be performed by any known adsorption cycle such as pressure swing, thermal swing, displacement purge or nonadsorbable purge, although pressure swing adsorption is preferred. However, this patent is silent as to specifics of the process, such as steps for treating the waste gas, nor is there disclosure of a high overall system recovery.

In general, first applications of PSA processes were performed to achieve the objective of removing smaller quantities of adsorbable components from essentially non-adsorbable gases. Examples of such processes are the removal of water from air, also called heatless drying, or the removal of smaller quantities of impurities from hydrogen. Later this technology was extended to bulk separations such as the recovery of pure hydrogen from a stream containing 30 to 90 mole percent of hydrogen and other readily adsorbable components like carbon monoxide or dioxide, or, for example, the recovery of oxygen from air by selectively adsorbing nitrogen onto molecular sieves.

The carrying out of the PSA processes in multi-bed systems is illustrated by the Wagner patent, U.S. Pat. No. 3,430,418, relating to a system having at least four beds. As is generally known and described in this patent, the PSA process is commonly performed in a cycle of a processing sequence that includes in each bed: (1) higher pressure adsorption with release of product effluent from the product end of the bed; (2) co-current depressurization to intermediate pressure with release of void space gas from the product end thereof; (3) countercurrent depressurization to a lower pressure; (4) purge; and (5) pressurization. The void space gas released during the co-current depressurization step is commonly employed for pressure equalization purposes and to provide purge gas to a bed at its lower desorption pressure.

Similar systems are known which utilize three beds for separations. See, for example, U.S. Pat. No. 3,738,087 to McCombs. The faster the beds perform steps 1 to 5 to complete a cycle, the smaller the beds can be when used to handle a given hourly feed gas flow. If two steps are performed simultaneously, the number of beds can be reduced or the speed of cycling increased; thus, reduced costs are obtainable.

U.S. Pat. No. 4,589,888 to Hiscock, et. al. discloses that reduced cycle times are achieved by an advantageous combination of specific simultaneous processing steps. The gas released upon co-current depressurization from higher adsorption pressure is employed simultaneously for pressure equalization and purge purposes. Co-current depressurization is also performed at an intermediate pressure level, while countercurrent depressurization is simultaneously performed at the opposite end of the bed being depressurized.

U.S. Pat. No. 4,512,780 to Fuderer discloses a pressure swing adsorption process with intermediate product recovery. Three products are recovered from a pressure swing adsorption process utilizing a displacement step in conjunction with pressure equalization between beds of a multi-bed adsorption system. This process is not cost efficient for the recovery of two products.

Although pressure swing separation adsorption (PSA) has been used to separate a wide variety of gases, the simple fact remains that there is no commercially practiced PSA process for the separation of nitrogen from methane. This is due to many factors including the lack of a nitrogen specific adsorbent and environmental regulations.

As previously pointed out, a significant percentage of U.S. natural gas reserves contain more than 4% nitrogen. The bulk of these reserves cannot be exploited because no economical technology exists for removing nitrogen especially at low flow rates, i.e., less than 25 MMSCFD process feed gas. Cryogenic distillation is the only process being used to date on any scale to remove nitrogen from methane in natural gas. Cryogenic plants are not used more widely because they are expensive and complicated and exhibit poor scale down economics.

It is the primary objective of this invention to provide a commercially viable PSA process for removing nitrogen from natural gas.

A further object of the invention is to provide a PSA process for removing nitrogen from natural gas, which can provide a highly concentrated methane product at high process efficiencies.

Another object of this invention is to separate nitrogen from natural gas by PSA and yield a methane product of high heat value.

Still another object of the invention is to provide and maintain peak efficiency of the nitrogen-selective adsorbent during PSA separation of nitrogen from natural gas.

SUMMARY OF THE INVENTION

This invention provides a novel PSA system to remove nitrogen from natural gas. The PSA processes of this invention to remove nitrogen from natural gas also achieves high system hydrocarbon recovery and usage of recovered hydrocarbons from the feed gas to provide additional heat value to the methane product stream. In accordance with this invention, a natural gas feed is first passed through an adsorbent selective for C3+ hydrocarbon components operating in a PSA cycle and directing the product gas leaving the first PSA system to a second PSA system containing an adsorbent selective for nitrogen. The methane-rich product stream of the second PSA is used to purge heavy hydrocarbons off the first PSA adsorbent. The heavy hydrocarbons add heat value to the methane product.

In another aspect of this invention, increased efficiency of the two-stage PSA process described above is provided by recycling a co-current intermediate pressure dump stream to the second stage PSA feed.

The PSA process for removing nitrogen from methane is also maintained to provide a high purity methane product by periodically heating an off-line nitrogen-selective adsorbent bed with methane product to drive off co-adsorbed methane and increase nitrogen adsorbent capacity.

DESCRIPTION OF THE INVENTION

As is known in the prior art, natural gas streams frequently contain components smaller than nitrogen, such as water vapor, carbon dioxide and hydrogen sulfide. The natural gas stream to be treated in accordance with the novel process of this invention preferably would have these polar contaminants removed prior to treatment.

The amount of nitrogen present in the natural gas stream to be treated is not critical in carrying out the novel process of this invention and can be as low as 1 mol percent or as high as about 50 mol percent. Typically, the nitrogen content is in the range of 5 to 20 mol percent.

In general, the first stage of the process involves the adsorptive removal of C3+ hydrocarbons from the nitrogen-containing natural gas stream. Thus, the feed stream is passed through a hydrocarbon-selective adsorbent, which adsorbs the heavier hydrocarbons, specifically propane, butane and heavier hydrocarbons. Removal of butane is especially useful. A desirable feature of the invention comprises the regeneration of the hydrocarbon-selective adsorbent bed by purging the bed with the product methane gas stream formed in the second stage PSA. The advantage of the two stage process is that the heavier hydrocarbons that would normally be adsorbed on the surface of the nitrogen-selective adsorbent and subsequently leave the PSA process as waste are now recovered into the sales gas. Thus, the BTU value of those hydrocarbons are added to the methane sales gas and not wasted.

The second stage PSA for adsorbing nitrogen from the natural gas stream contains process steps not found in typical PSA processes. The nitrogen-removal, second stage PSA includes a co-current low pressure dump step and recycle of the low pressure stream to the feed of the second stage PSA which contains the nitrogen-selective adsorbent. Recycle steps in many PSA systems are often referred to as rinse steps and consist of recycling waste gas back to the feed. However, compression requirements for recycling waste gas to feed pressure are significantly higher than the recycle of this invention as the typical waste stream is available at 7 psia, while the co-current dump gas stream is available at a higher pressure of about 40 psia. Those skilled in the art will recognize that compression requirements scale with the inverse of the suction pressure. An additional, novel feature of the second stage PSA process of this invention includes a thermal regeneration of the nitrogen-selective adsorbent. It has been found that by heating the adsorbent bed with methane product while the bed is offline and then cooling under a stream consisting of predominantly nitrogen it is possible to improve nitrogen adsorption performance back to the original fresh performance.

Figure 1:
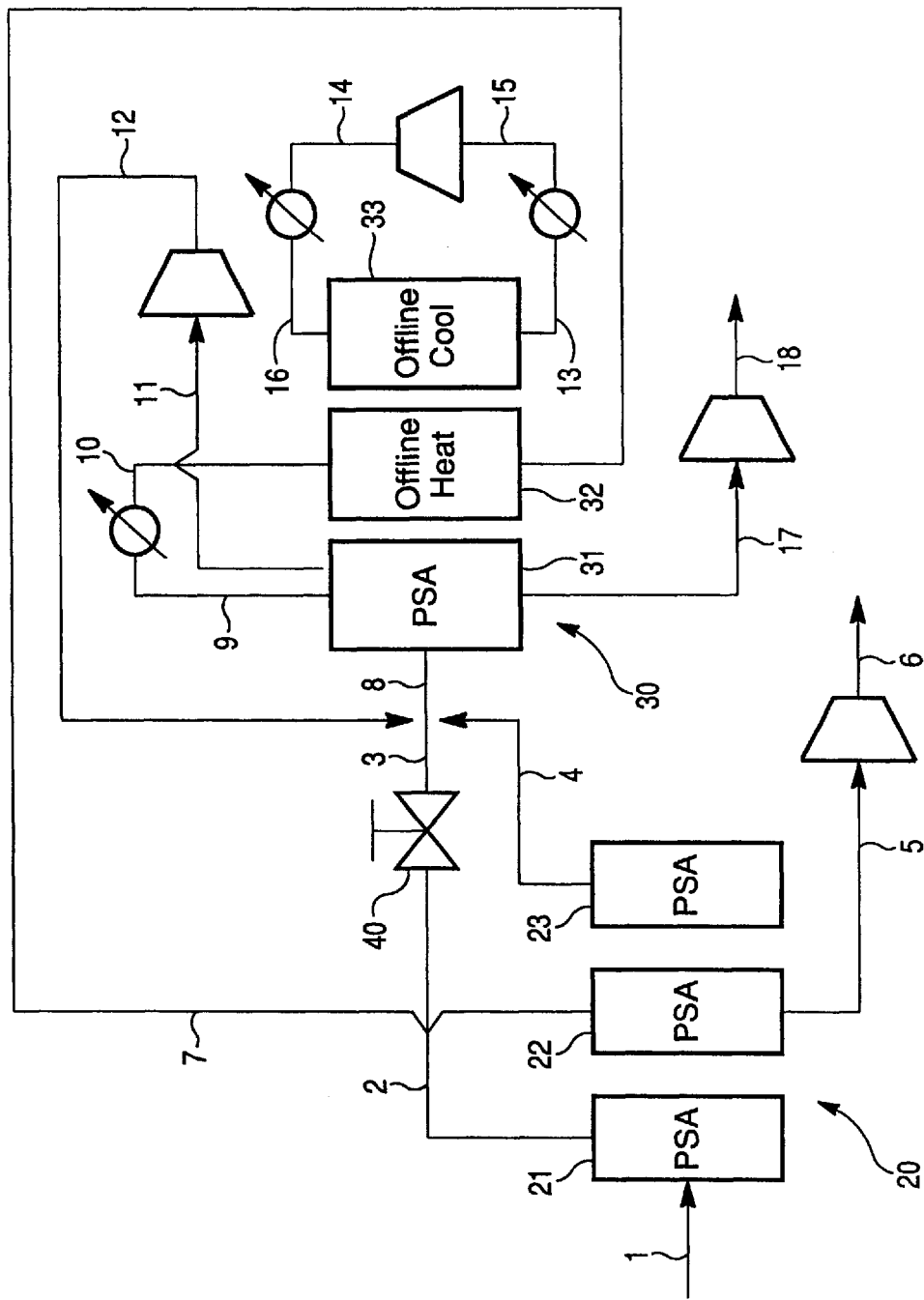
FIG. 1 represents the integrated PSA process of this invention for removing nitrogen from natural gas.

The two PSA processes described above, i.e., heavy hydrocarbon adsorption and subsequent nitrogen adsorption can be integrated as shown in FIG. 1. In FIG. 1, each of the PSA stages is shown with three columns. Each column shown merely represents a different step in the process of this invention. The columns shown do not necessarily depict the actual number of columns used in the apparatus design. In fact, the process steps of each PSA can be accomplished with one or a series of multiple beds operating in parallel during adsorption, desorption, and intermediate pressurization/depressurization (equalization) steps.

An overview of the process of this invention can be described by referring to FIG. 1. As shown, raw natural gas stream 1 enters the first stage PSA, represented by reference numeral 20. Stream 1 typically will contain over 5 mol % nitrogen. The process steps of PSA 20 can be described by referring to columns 21, 22 and 23. Column 21 represents the adsorption step. In this step, natural gas feed stream 1 enters a column 21, which contains a bed of adsorbent, which selectively adsorbs C3+ hydrocarbons from the natural gas stream 1. Preferably, an adsorbent is chosen to remove substantially all of the butane and, higher hydrocarbons from natural gas feed stream 1. A product natural gas stream 2 leaves column 21 and is reduced in pressure to a lower pressure feed stream 3. Stream 4 is a product natural gas stream produced during a co-current depressurization step of the adsorbent bed. This step is depicted as column 23.

Streams 3 and 4 are combined to form a portion of feed 8 to second stage PSA 30 depicted as beds 31, 32, and 33, which represent, respectively, nitrogen adsorption/desorption, offline heat regeneration of the adsorbent and offline cooling of the adsorbent. Feed stream 8 is a natural gas stream, which has a reduced C3+ hydrocarbon content and is a combination of streams 3, 4 and recycle stream 12. Feed 8 is passed through a nitrogen-selective adsorbent in column 31. Stream 9 is the methane-rich product stream, which leaves the adsorbent bed represented by column 31. After leaving bed 31 product stream 9 is heated to form stream 10 and stream 10 is used to heat the nitrogen-selective adsorbent in offline vessel 32 to a temperature sufficient to regenerate the adsorbent. A temperature of at least about 200° F., preferably at least 300° F. is capable of desorbing co-adsorbed methane and regenerating the nitrogen adsorption capacity, which has been found to decrease with time. The waste gas of PSA 30 is nitrogen-rich stream 17. Stream 17 leaves the PSA 30 during depressurization/desorption of the adsorbent bed in column 31 to a low pressure of 5–10 psia, and is then compressed to form waste stream 18. Gas stream 11 is produced during co-current desorption of the adsorbent bed in column 31. Stream 11 is compressed to feed pressure as stream 12 and recycled entirely back to feed for PSA 30. Stream 12 joins streams 3 and 4 to form feed 8 to PSA 30. After the offline bed in column 32 has been heated in the countercurrent direction to the feed to process 30 with stream 10 and has reached effective temperature for desorption of methane, the bed is cooled by recirculating nitrogen as depicted in column 33. Cooling is provided for stream 13 before entering the suction of the compressor at stream 15 and additional cooling from compression is provided at stream 14 to stream 16. Cooling may be done either cocurrrent or countercurrent to the feed direction of process 30. Cooling in the cocurrent direction is advantageous if water and/or carbon dioxide are present in the feed. It has been found that water and carbon dioxide may not be fully removed during the off-line heating step. By cooling cocurrently, the water and/or carbon dioxide are transported down the bed. Conversely, if the bed were cooled countercurrently, the water and/or carbon dioxide would be absorbed at the product end of the bed, where it would be expected to degrade performance. However, if water and/or carbon dioxide are not present, it is preferable to cool countercurrently to avoid lifting the bed by cooling at too fast a rate. We assume for the above discussion that process 30 is fed from the bottom of the bed. Finally, methane-rich stream 7 subsequent to regenerating the 5,adsorbent in column 32, is recycled to column 22 and used to purge C3+ hydrocarbons, which have been adsorbed during the first stage PSA 20. The product gas rich in methane and now containing the C3+ hydrocarbon adsorbed in PSA 20 leaves the adsorbent bed as depicted by column 22 via stream 5 and stream 5 is compressed to a high heat value sales gas as stream 6.

More specific process parameters are now given with respect to the operation of the process of this invention. Again, referring to FIG. 1, PSA 20 can be described as the BTU recovery PSA since C3+ hydrocarbon heat values which would be coadsorbed on the nitrogen-selective adsorbent are first separated before nitrogen adsorption and then added to the methane-rich product subsequent to nitrogen adsorption. PSA 20 consists of four basic steps. In step 1, column 21 containing the hydrocarbon selective adsorbent is fed natural gas stream 1 which is at an elevated pressure of 100 to 1200 psia, preferably, 200 to 800 psia. The product gas, stream 2, leaving the adsorbent bed in this step is then throttled via valve 40 to the operating pressure of the second stage or nitrogen adsorption PSA 30 for a period of 10 seconds to 10 minutes. Operating pressure of PSA 30 is at a reduced pressure of 50–800 psia, preferably, 100–500 psia. Upon completion of the C3+ hydrocarbon adsorption step, the bed (as depicted in column 23) is co-currently depressurized to the operating pressure of PSA 30 to form stream 4. All of the gas leaving the adsorbent bed during the adsorption and co-current depressurization steps (streams 2 and 4) is sent on to PSA 30. Preferably, there are no pressure equalization steps between adsorption beds. Stream 2 which is at gas feed pressure of PSA 20 is throttled to feed pressure of PSA 30. Stream 4 produced by co-current depressurization of the adsorbent bed is at PSA 30 feed pressure. Next, the adsorbent bed as depicted in column 22 is purged with the methane-rich product gas produced from the nitrogen adsorption PSA 30. During the purging step, the C3+ hydrocarbons which have been adsorbed during the hydrocarbon adsorption step are removed or desorbed from the adsorbent and leave PSA 20 mixed with the sales gas via streams 5 and 6.

Operation of PSA 30 involves the following steps: adsorption, equalization, co-current depressurization to compression, provide purge, fuel, countercurrent depressurization, purge, equalization and pressurization. These steps are well-known to those of ordinary skill in this art. Reference is again made to U.S. Pat. Nos. 3,430,418; 3,738,087 and 4,589,888 for a discussion of these internal steps of a PSA process. The nitrogen adsorption process, PSA 30, begins with the nitrogen adsorption step in which gas stream 8 is fed to a bed containing a nitrogen selective adsorbent, depicted as column 31. Nitrogen adsorption yields a product stream 9 rich in methane, reduced in nitrogen and at approximately the same operational pressure as feed 8. After the adsorption step, the bed is co-currently depressurized in a series of steps referred to in the art as equalizations. After the adsorbent bed has completed 1 to 4 equalizations, the adsorbent bed can be further co-currently depressurized. The gas leaving the bed during the co-current depressurization, depicted as stream 11 can be used as either fuel, provide purge, recycled back to feed or any combination thereof. Stream 11 will have a pressure of 10 to 100 psia, preferably 20 to 60 psia. Subsequently, the bed is counter-currently depressurized, and then purged with gas from the earlier provide purge step. The adsorbent bed is pressurized with gas from earlier equalizations, and finally the bed is pressurized with product gas or alternatively feed gas. These steps are routine, and except for recycling the co-current intermediate pressure dump stream 11 to feed stream 8 are known in the art. This latter step is unique and important for overall process efficiency including improvement in operational costs. By using a co-current dump stream for recycle instead of the typical waste stream recycle, operational energy costs (compression costs) are saved as the dump stream 11 is compressed to PSA 30 feed pressure from a higher pressure than the waste stream. Subsequent to recycling the dump stream 11, a further depressurization/equalization step to about 20 psia can be performed to recover methane values from void space gas before a final purge to waste gas at low pressure, e.g. 7 psia. Without the further depressurization/equalization, valuable methane gas would be purged to waste 17/18.

Figure 2:
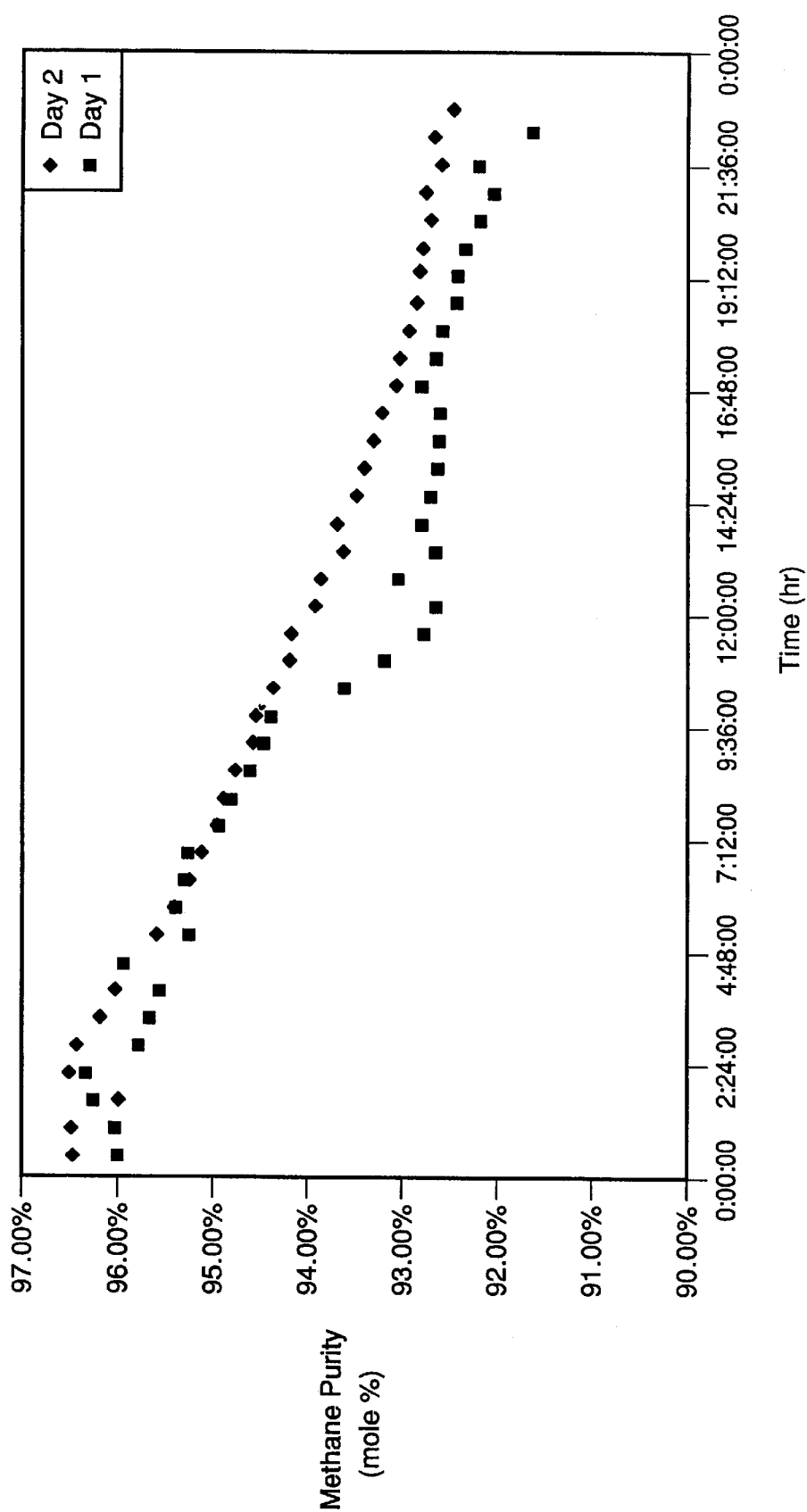
FIG. 2 illustrates the performance degradation of the nitrogen-adsorbent over time and the rejuvenation of the bed after heating the bed under flowing methane. DETAILED

It has been found that the performance of the nitrogen-selective PSA 30 varies over time. After an initial 1 hour start-up period, PSA 30 starts producing a higher purity methane product stream than the average purity. Subsequently, methane purity in the product stream 9 steadily drops. After 12 hours the purity of the product stream drops below 94% purity. This phenomenon of a gradual degradation in performance is illustrated in FIG. 2. FIG. 2 shows the methane product purity vs. time for a fixed feed flow rate. As can be seen in FIG. 2, the product purity vs. time steadily drops.

Periodically heating the bed increases the nitrogen working capacity (amount of nitrogen adsorbed/desorbed each cycle) of PSA 30. It is believed that this is accomplished by lowering the methane loading on the adsorbent. The loss in nitrogen working capacity is illustrated by the lowering of product purity at a fixed product draw rate. This performance decline vs. time can be mitigated by periodically heating/cooling a bed(s) in PSA 30 as illustrated in FIG. 1. As shown therein, a high-pressure methane stream 10 is used to heat the sorbent in PSA 30 to about 300°F. for 1.5 hours. PSA 30 is then cooled for 1.5 hours to 70° F. with nitrogen. After the cooling period is completed, the adsorbent bed in PSA 30 is again fed feed gas. Referring again to FIG. 2, it can be seen that subsequent to the heating and cooling cycle, the purity of the methane product at day 2 jumps to the methane purity levels on day 1.

To accomplish regeneration of the nitrogen-selective adsorbent, two vessels are always "off-line", one heating (column 32), one cooling (column 33). Heating the vessel 32 is accomplished at PSA 30 feed pressure by heating product gas 9 from column 31 (using cross exchangers and a heater) and passing resultant heated product gas stream 10 through vessel 32. Cooling is preferentially done under nitrogen at low pressure. Pressure left in vessel 32 is equalized (one cycle only) and then inserted into a nitrogen recycle loop 13, 14, 15, 16 as vessel 33. Not illustrated is a "nitrogen-generator" which takes part of the low pressure waste gas 17 and uses a simple 2-bed PSA design using carbon adsorbent to extract the nitrogen. This nitrogen is fed into the recycle loop equipped with a purge to purge out lo methane from the heating step. The low pressure waste stream of the 2-bed PSA is sent to the waste header of process 30. When cool, the vessel is brought back on-line replacing a "spent" vessel at the same low pressure.

PSA 20 for removal of C3+ hydrocarbon from natural gas and PSA 30 for removal of nitrogen from natural gas can be operated under conditions of either rate selectively or equilibrium selectivity. Rate selectivity is defined as to assume that equal concentrations of component A and B exist above a clean adsorbent at time zero. If component A adsorbs at a faster rate than component B then the adsorbent is rate selective for component A. Equilibrium selectivity is defined as to assume that equal concentrations of component A and B exist above an adsorbent and further both the adsorbed phase concentration and the gas phase concentration are not changing as a function of time. If component A adsorbs to a higher concentration in the adsorbed phase than component B then the adsorbent is equilibrium selective for component A. Depending on the adsorbent used, adsorption/desorption cycle times can be adjusted to provide rate or equilibrium selectivity.

The C3+ hydrocarbon selective adsorbent used in the first stage PSA 20 is either a crystalline aluminosilicate zeolite such as 13X or a high aluminum X having a silicon-to-aluminum ratio of about 1 or an amorphous adsorbent such as silica gel or carbon. It is preferred to employ the silica gel adsorbent which under equilibrium conditions selectivity adsorbs the C3+ hydrocarbons and not the methane from the raw feed. A particularly preferred silica gel is Sorbead® AF125 available from Engelhard Corp.

The nitrogen selective crystalline zeolites utilized in the second stage PSA 30 are preferably CTS-1 zeolites described and claimed in the U.S. Pat. No. 6,068,682, issued May 30, 2000 and assigned to Engelhard Corp. A barium exchanged ETS-4 described and claimed in U.S. Pat. No. 5,989,316, issued Nov. 23, 1999 and, again assigned to present assignee Engelhard Corp., can also be used as an effective nitrogen selective adsorbent for natural gas.

The CTS-1 zeolites are characterized as having a pore size of approximately 3–4 Angstrom units and a composition in terms of mole ratios of oxide as follows:

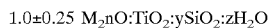

1.0±0.25 M$_2$nO:TiO$_2$:ySiO$_2$:zH$_2$O wherein M is at least one cation having a valence n, y is from 1.0 to 100 and z is from 0 to 100, said zeolite being characterized by the following X-ray diffraction pattern.

| D-spacings (Angstroms) | I/I$_0$ |
| --- | --- |
| 11.3 ± 0.25 | Very Strong |
| 6.6 ± 0.2 | Medium-Strong |
| 4.3 ± 0.15 | Medium-Strong |
| 3.3 ± –.1 | Medium-Strong |
| 2.85 ± 0.05 | Medium-Strong | wherein very strong equals 100, medium-strong equals 15–80.

The CTS-1 materials are titanium silicates which are ifferent than conventional aluminosilicate zeolites. The titanium silicates useful herein are crystalline materials formed of octahedrally coordinated titania chains which are linked by tetrahedral silica webs. The CTS-1 adsorbents are formed by heat treating ETS-4 which is described in U.S. Pat. No. 4,938,939, issued Jul. 3, 1990 and assigned to Engelhard Corp. U.S. Pat. Nos. 4,938,939; 5,989,316; and 6,068,682 are herein incorporated by reference.

Barium ETS-4 is ETS-4, which has been exchanged with barium, such that barium represents at least 30% of the exchangeable cations of ETS-4.

As is known in the PSA art, the zeolite sorbents can be composited or grown in-situ with materials such as clays, silica and/or metal oxides. The latter may be either naturally occurring or in the form of gelatinous precipitates or gels including mixtures of silica and metal oxides. Normally crystalline materials have been incorporated into naturally occurring clays, e.g., bentonite and kaolin, to improve the crush strength of the sorbent under commercial operating conditions. These materials, i.e., clays, oxides, etc., function as binders for the sorbent. It is desirable to provide a sorbent having good physical properties because in a commercial separation process, the zeolite is often subjected to rough handling which tends to break the sorbent down into powder-like materials which cause many problems in processing. These clay binders have been employed for the purpose of improving the strength of the sorbent.

Naturally occurring clays that can be composited with the crystalline zeolites include the smectite and kaolin families, which families include the montmorillonites such as sub-bentonites and the kaolins known commonly as Dixie, McNamee, Georgia and Florida or others in which the main constituent is halloysite, kaolinite, dickite, nacrite or anauxite. Such clays can be used in the raw state as originally mined or initially subjected to calcinations, acid treatment or chemical modification.

In addition to the foregoing materials, the crystalline zeolites may be composited with matrix materials such as silica-alumina, silica-magnesia, silica-zirconia, silicathoria, silica-berylia, silica-titania as well as ternary compositions such as silica-alumina-thoria, silica-aluminazirconia, silica-alumina-magnesia and silica-magnesiazirconia. The matrix can be in the form of a cogel. The relative proportions of finally divided crystalline metal organosilicate and inorganic oxide gel matrix can vary widely with the crystalline organosilicate content ranging from about 5 to about 90 percent by weight and more usually in the range of 90 percent by weight of the composite.

Prior to being used, the adsorbents are thermally treated as is well-known in the art.

If carbon or silica gel is used as the PSA 20 adsorbent, they need not be composited with the aforementioned materials.

EXAMPLE 1

Preparation of CTS-1 Beads

I. ETS-4 Molecular Sieve Synthesis:

a. Gel Preparation: A caustic solution was prepared by blending together 2,600 lbs. of DI water, 6,806 lbs. of N-Clear sodium silicate (28.7% SiO$_2$/8.93% Na$_2$O) and 6,766 lbs. of sodium hydroxide solution (38.6 % Na$_2$O) in a stirred 4,000 gal tank. An acidic solution of equal volume was prepared by blending together 3,819 lbs. of Di water, 8,395 lbs. of titanium sulfate solution (10.3% TiO$_2$/36.7% H$_2$SO$_4$) and 631 lbs. of sulfuric acid (96.7% H$_2$SO$_4$) in a second stirred 4,000 gal tank. These two solutions were then simultaneously added at ~10 gpm each into a 100 gal stirred (1,300~rpm) strike tank. The resulting gel was pumped into a 5,000 gal holding tank at a rate which maintained ~70 gal of gel in the strike tank.

b. Gel Crystallization to ETS-4: 900 lbs. of the above gel were added to a stirred (~75 rmp) 100 gal titanium clad stainless steel (SS) autoclave then reacted at 215° C. for 24 hours. 452 lbs. of the resulting product slurry were filtered on a 1.2 ft$^3$ plate and frame filter press then washed with 75 gal of Di water at 170° F. This initially washed cake was then reslurried (at ~50 rpm) in 75 gal of Di water in a 100 gal SS reactor and heated to 170° F. for 15 minutes. The reslurry was filtered on the plate and frame filter press then finally washed with 150 gal of Di water at 170° F. This washed ETS-4 cake (18.5% Na$_2$O/54.2% SiO$_2$/27.8% TiO$_2$) was then strontium exchanged as follows:

II. Preparation of Strontium Exchanged ETS-4 Molecular Sieve (CTS-1):

7.84 kg of SrCl$_2$.6H$_2$O was dissolved in 34 gal of DI water in the 100 gal SS reactor. To this solution was added 39.7 kg of the above ETS-4 filter cake which equals 15.7 kg ETS-4 on a dry basis (as determined by an Ohaus moisture analyzer (Model #6010PC). While stirring at ~50 rpm, this exchange slurry was reacted at 170° F. for 90 minutes. The resulting product slurry was filtered on the 1.2 ft$^3$ plate and frame filter press then washed with 150 gal of DI water at 170° F. This washed (Sr/Na) ETS-4 cake (4.37% Na$_2$O/20.3% SrO/50.7% SiO$_2$/23.3% TiO$_2$) was then dried at 110° C.

III. Preparation of Dense 10% Bentonite Bound Beads (−12/+ 40 Mesh)

1,715 g of the above (Sr/Na) ETS-4 dried cake were added to the bowl of a 12"diameter Eirich blender (Model #R02). This equals 1,650 g (dry basis) as determined by an Ohaus moisture analyzer (Model #6010PC). Next, 196.1 g of bentonite clay powder (Volclay SPV 200) were added to the Eirich bowl. This equals 156.9 g (dry basis) as determined by the Ohaus moisture analyzer. These two dry powders were then mixed for ~10 minutes on the low rotation setting #I and low agitation setting #I.

DI water was then added to the blended powder while still mixing on the low rotation and agitation settings. The water was added a portion at a time, with reduced amounts being added as the mixture got "wetter". The total amount of water added was 1,550 g. The bowl was then rotated on the high setting #II until mostly "oversized", i.e., >+12 mesh sized, product was obtained. Occasionally, the agitator was turned on (at the low setting #I) to reduce larger chunks. The resulting "oversized" beads were dried at 110° C. overnight, then reworked as follows:

DI water was added to the dried beads while mixing on the low rotation and agitation settings. Again, the water was added a portion at a time, with reduced amounts being added as the mixture got "wetter". 1,260 g of water was added during this step. The bowl was then rotated on the high setting #II until mostly −12/+40 mesh product was obtained. Occasionally, the agitator was turned on (at the low setting #I) to reduce the larger beads. "Oversized" beads were separated by screening with a 12 mesh screen then reworked. When the entire product passed through the 12 mesh screen, it was dried overnight at 100° C. The dried beads were then classified using 12 and 40 mesh screens. The total weight of dried −12/+40 mesh beads obtained was 1,196 g.

IV. Calcination to CTS 1,196 g. of bounded material is placed in a fixed bed. The bed is fed with air that has been dried to a dew point of −45° F. The temperature is ramped from ambient temperature to 260° C. in 1 hour. 260° C. air is then fed to the bed for 10–12 hours. After the bed has been heated for 10–12 hours, it is cooled with air at ambient temperature having a dew point of −45° F. and a $CO_2$ content less than 2 ppm. Cooling is completed in approximately 6–8 hours and then the airflow is terminated.

EXAMPLE 2

In this Example, a pilot plant study was conducted using the process of the present invention to remove nitrogen from a natural gas feed stream. The pilot plant study was conducted in two separate steps. A synthetic feed 1 and a synthetic feed 8 were made and the respective pilot plants for PSA 20 and PSA 30 were run in accordance with the process streams as shown in FIG. 1. The feed stream 7 to PSA 20 was a synthetic feed having the composition essentially identical to stream 10. The C3+ hydrocarbon sorbent used for PSA 20 was a silica gel, Sorbead® AF125 from Engelhard Corporation. The nitrogen-selective absorbent was a CTS-1 titanium silicate as prepared in Example 1. A first material balance around the C3+ hydrocarbon PSA 20 and a second material balance around the nitrogen-selective PSA 30 are shown in Table 1. The temperature, pressure, molar flow and composition of each of the streams as set forth in FIG. 1 are provided in Table 1.

TABLE 1

| Stream No. | 1 | 2 | 3 | 4 | 5 | 6 | 7 | 8 | 9 |
|---|---|---|---|---|---|---|---|---|---|
| Temperature (F.) | 100 | 100 | 75 | 75 | 104.6 | 202.8 | 105 | 86.97 | 105 |
| Pressure (psia) | 700 | 700 | 400 | 400 | 400 | 700 | 400 | 400 | 400 |
| Molar Flow (lbmole/hr) | 32.94 | 25.245 | 25.245 | 8.415 | 28.75 | 28.75 | 29.46 | 37.31 | 29.46378 |

| Component (Mole) | 1 | 2 | 3 | 4 | 5 | 6 | 7 | 8 | 9 |
|---|---|---|---|---|---|---|---|---|---|
| (Methane) | 0.8565 | 0.8795 | 0.8795 | 0.8795 | 0.9166 | 0.9166 | 0.9414 | 0.8545 | 0.941448 |
| (Ethane) | 0.0296 | 0.0241 | 0.0241 | 0.0241 | 0.0275 | 0.275 | 0.0212 | 0.278 | 0.02116 |
| (Propane) | 0.0079 | 0.0023 | 0.0023 | 0.0023 | 0.0077 | 0.0077 | 0.0013 | 0.0034 | 0.001299 |
| (n-Butane) | 0.0027 | 0 | 0 | 0 | 0.0031 | 0.0031 | 0 | 0 | 0 |
| (Nitrogen) | 0.1 | 0.093 | 0.093 | 0.093 | 0.0416 | 0.0416 | 0.035 | 0.1133 | 0.035 |
| ($CO_2$) | 0.0005 | 0 | 0 | 0 | 0.0006 | 0.0006 | 0 | 0 | 0 |
| ($H_2O$) | 0.0001 | 0 | 0 | 0 | 0.0001 | 0.0001 | 0 | 0 | 0 |
| (Helium) | 0.0011 | 0.0011 | 0.0011 | 0.0011 | 0.0011 | 0.0011 | 0.0011 | 0.001 | 0.001093 |
| (n-Pentane) | 0.0011 | 0 | 0 | 0 | 0.0012 | 0.0012 | 0 | 0 | 0 |
| (n-Hexane) | 0.0004 | 0 | 0 | 0 | 0.0005 | 0.0005 | 0 | 0 | 0 |

| Stream No. | 10 | 11 | 12 | 13 | 14 | 15 | 16 | 17 | 18 |
|---|---|---|---|---|---|---|---|---|---|
| Temperature (F.) | 300 | 120 | 100 | 300 | 170 | 120 | 120 | 80 | 170 |
| Pressure (psia) | 400 | 40 | 400 | 30 | 40 | 28 | 28 | 7 | 15 |
| Molar Flow (lbmole/hr) | 29.46378 | 3.653 | 3.653 | 3.653 | 3.653 | 3.653 | 3.653 | 4.194356 | 4.194356 |

| Component (Mole) | 10 | 11 | 12 | 13 | 14 | 15 | 16 | 17 | 18 |
|---|---|---|---|---|---|---|---|---|---|
| (Methane) | 0.941448 | 0.624 | 0.624 | 0 | 0 | 0 | 0 | 0.444689 | 0.444689 |
| (Ethane) | 0.02116 | 0.0626 | 0.0626 | 0.05 | 0.05 | 0.05 | 0.05 | 0.044592 | 0.044592 |
| (Propane) | 0.001299 | 0.0134 | 0.0134 | 0 | 0 | 0 | 0 | 0.009582 | 0.009582 |
| (n-Butane) | 0 | 0 | 0 | 0 | 0 | 0 | 0 | 0 | 0 |
| (Nitrogen) | 0.035 | 0.3 | 0.3 | 0.95 | 0.95 | 0.95 | 0.95 | 0.500284 | 0.500284 |
| ($CO_2$) | 0 | 0 | 0 | 0 | 0 | 0 | 0 | 0 | 0 |
| ($H_2O$) | 0 | 0 | 0 | 0 | 0 | 0 | 0 | 0 | 0 |
| (Helium) | 0.001093 | 0 | 0 | 0 | 0 | 0 | 0 | 0.000853 | 0.000853 |
| (n-Pentane) | 0 | 0 | 0 | 0 | 0 | 0 | 0 | 0 | 0 |
| (n-Hexane) | 0 | 0 | 0 | 0 | 0 | 0 | 0 | 0 | 0 |

Once given the above disclosure, many other features, modifications, and improvements will become apparent to the skilled artisan. Such other features, modifications, and improvements are, therefore, considered to be a part of this invention, the scope of which is to be determined by the following claims.

We claim:

1. A pressure swing absorption (PSA) process for the separation of nitrogen from a mixture of the same with methane which comprises:
   (a) passing a feed stream comprising said mixture in contact with a nitrogen-selective sorbent in a PSA unit so as to preferentially adsorb nitrogen and produce a methane-rich product stream containing at least 70 mol. % methane and a low pressure purge stream having a higher molar concentration of nitrogen than said mixture; and
   (b) subsequent to step (a), periodically heating said nitrogen-selective sorbent with the methane-rich product stream to drive off accumulated methane from such sorbent.

2. The process of claim 1, wherein subsequent to step (b), cooling said nitrogen-selective sorbent.

3. The process of claim 2, wherein said nitrogen-selective sorbent is cooled by contact with a gas stream which contains at least 30 mole % nitrogen.

4. The process of claim 3, wherein said nitrogen-selective sorbent is cooled with a gas stream containing at least 90 mole % nitrogen.

5. The process of claim 4, wherein said stream to cool said nitrogen-selective sorbent comprises at least 90% nitrogen with the balance methane.

6. The process of claim 2, wherein said cooling is provided by contacting said nitrogen-selective sorbent with a gas stream fed countercurrent to the direction of said feed stream.

7. The process of claim 6, wherein said feed stream does not contain water or carbon dioxide.

8. The process of claim 2, wherein said cooling is provided by contacting said nitrogen-selective sorbent with a gas stream fed co-current to the direction of said feed stream.

9. The process of claim 8, wherein said feed stream contains water and/or carbon dioxide.

10. The process of claim 1, wherein said nitrogen-selective sorbent is a CTS-1 crystalline titanium silicate having a pore size of 3 to less than 4 Å.

11. The process of claim 1, wherein said nitrogen-selective sorbent is a barium exchanged ETS-4 crystalline titanium silicate wherein barium comprises at least 30% of the exchangeable cations of said titanium silicate.

12. The process of claim 1 comprising co-currently depressurizing said PSA unit to form a recycle stream rich in methane, said recycle stream having a pressure less than said methane-rich product stream, but greater than said purge stream, recycling said recycle stream to said feed stream.

13. The process of claim 1, wherein said feed stream comprises natural gas.

14. A process for the separation of nitrogen and hydrocarbons from a natural gas stream, which comprises:
   passing said natural gas stream to a first pressure swing adsorption unit containing a hydrocarbon-selective sorbent so as to preferentially adsorb at least C4+ hydrocarbons to produce a first product stream comprising methane, nitrogen and a reduced level of said hydrocarbons relative to said natural gas stream; and
   passing said first product stream to a second pressure swing absorption unit containing a nitrogen-selective sorbent so as to preferentially adsorb nitrogen and produce a second product stream enriched with methane and a low pressure purge stream having a higher molar concentration of nitrogen than said first product stream.

15. The process of claim 14 comprising; passing said second product stream in contact with said hydrocarbon-selective sorbent subsequent to formation of said first product stream so as to adsorb said C4+ hydrocarbons into said second product stream.

16. The process of claim 14, wherein said hydrocarbon-selective sorbent preferentially adsorbs C3+ hydrocarbons.

17. The process of claim 14 comprising co-currently pressurizing said first pressure swing adsorption unit to form a lower pressure product stream, combining said first product stream and said lower pressure product stream to form a combined stream and contacting said combined stream with said nitrogen-selective sorbent.

18. The process of claim 17, wherein the pressure of said first product stream is reduced to the pressure of said lower pressure product stream prior to said combining.

19. The process of claim 14 comprising co-currently depressurizing said second pressure swing adsorption unit to form a low pressure recycle stream having a pressure lower than said second product stream and higher than said purge stream, combining said low pressure recycle stream with said first product stream to form a first combined recycle stream and passing said first combined recycle stream in contact with said nitrogen selective sorbent.

20. The process of claim 19 comprising co-currently depressurizing said first PSA unit to form a lower pressure product stream, combining said first product stream, said lower pressure product stream and said low pressure recycle stream to form a second combined recycle stream and contacting said second combined recycle stream with said nitrogen-selective sorbent.

21. The process of claim 20, wherein the pressure of said first product stream is lowered to the pressure of said lower pressure product stream and the pressure of said low pressure recycle stream is raised to the pressure of said lower pressure product stream prior to combining.

22. The process of claim 19, wherein the pressure of said low pressure recycle stream is raised and the pressure of said first product stream is lowered so that said low pressure recycle stream and said first product stream are at the same pressure prior to combining.

23. The process of claim 19, comprising equalizing the pressure of said second PSA subsequent to forming said low pressure recycle stream and prior to forming said purge stream.

24. The process of claim 14, wherein said hydrocarbon-selective sorbent is silica.

25. The process of claim 24, wherein said nitrogen-selective sorbent is CTS-1 titanium silicate having a pore size of about 3 to less than 4 Å.

26. The process of claim 14, wherein said nitrogen-selective sorbent is CTS-1 titanium silicate having a pore size of about 3 to less than 4 Å.

27. The process of claim 14 comprising periodically heating said nitrogen-selective sorbent subsequent to formation of said second product stream and said purge stream to drive off accumulated methane from said nitrogen-selective sorbent.

28. The process of claim 27, comprising heating said second product stream to form a heated second product stream and passing said heated second product stream in contact with said nitrogen-selective sorbent so as to heat said nitrogen-selective sorbent.

29. The process of claim 28, wherein said second product stream is heated to a temperature of at least about 200° F.

30. The process of claim 28 comprising passing said second product stream subsequent to heating said nitrogen-selective sorbent into contact with said hydrocarbon-selective sorbent.

31. The process of claim 14, wherein said nitrogen-selective sorbent is barium exchanged ETS-4 titanium silicate wherein barium represents at least 30% of the exchangeable cations on said titanium silicate.

32. The process of claim 14, wherein said natural gas stream contains over 4 mole % nitrogen.

33. The process of claim 14, wherein said first product stream is essentially devoid of C4+ hydrocarbon.

34. The process of claim 33, wherein said first product stream has reduced levels of propane relative to said natural gas stream.

35. A pressure swing absorption (PSA) process for the separation of nitrogen from a mixture of the same with methane which comprises:

(a) passing a feed stream comprising said mixture in contact with a nitrogen-selective sorbent in a PSA unit so as to preferentially adsorb nitrogen and produce a methane-rich product stream containing at least 70 mol. % methane and a low pressure purge stream having a higher molar concentration of nitrogen than said mixture; and (b) co-currently depressurizing said PSA unit to form a recycle stream rich in methane, said recycle stream having a pressure less than said methane-rich product stream, but greater than said purge stream, recycling said recycle stream to said feed stream.

36. The process of claim 35, wherein said feed stream comprises natural gas.

37. The process of claim 35, wherein said nitrogen-selective sorbent is a CTS-1 crystalline titanium silicate having a pore size of 3 to less than 4 Å.

38. The process of claim 35, wherein said nitrogen-selective sorbent is a barium exchanged ETS-4 crystalline titanium silicate wherein barium comprises at least 30% of the exchangeable cautions of said titanium silicate.

* * * * *

UNITED STATES PATENT AND TRADEMARK OFFICE
CERTIFICATE OF CORRECTION

PATENT NO. : 6,444,012 B1
DATED : September 3, 2002
INVENTOR(S) : Dolan et al.

It is certified that error appears in the above-identified patent and that said Letters Patent is hereby corrected as shown below:

Column 14,
Line 16, change "pressurizing" to -- depressurizing --.

Signed and Sealed this

Fourth Day of February, 2003

JAMES E. ROGAN
*Director of the United States Patent and Trademark Office*